(12) United States Patent
Perry et al.

(10) Patent No.: US 8,214,022 B2
(45) Date of Patent: Jul. 3, 2012

(54) HYSTEROGRAPHY AND INTRAUTERINE VENOGRAPHY CATHETER

(75) Inventors: C. Paul Perry, Birmingham, AL (US); Richard P. Marvel, Baltimore, MD (US); Benjamin T. Biltz, Bloomington, IN (US); Rodney W. Bosley, Jr., Chester Springs, PA (US); Jessica Watts Miller, St. Louis, MO (US); Troy W. Wingler, Martinsville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1415 days.

(21) Appl. No.: 11/820,078

(22) Filed: Jun. 18, 2007

(65) Prior Publication Data

US 2008/0039726 A1 Feb. 14, 2008

Related U.S. Application Data

(60) Provisional application No. 60/816,719, filed on Jun. 27, 2006.

(51) Int. Cl.
*A61B 6/00* (2006.01)
(52) U.S. Cl. .................................................. 600/431
(58) Field of Classification Search .................. 600/431
See application file for complete search history.

(56) References Cited

U.S. PATENT DOCUMENTS

| | | | |
|---|---|---|---|
| 3,356,089 A | 12/1967 | Francis | |
| 3,884,220 A | 5/1975 | Hartnett | |
| 5,081,997 A | 1/1992 | Bosley, Jr. et al. | |
| 5,289,831 A | 3/1994 | Bosley | |
| 5,823,363 A * | 10/1998 | Cassel | 211/60.1 |
| 6,706,026 B1 | 3/2004 | Goldstein et al. | |
| 2003/0009128 A1 | 1/2003 | Ackerman et al. | |
| 2006/0135962 A1 | 6/2006 | Kick et al. | |

OTHER PUBLICATIONS

International Search Report of International Application No. PCT/US2007/014217, dated Dec. 11, 2007 (6 pages).
Written Opinion of the International Searching Authority for International Application No. PCT/US2007/014217, dated Dec. 11, 2007 (12 pages).
Confino, E., "Tubal Cannulation for the Diagnosis and Treatment of Proximal Tubal Occlusion," Cook®, Cook Urological Incorporated 2000, 8 pages.
Perry, Paul, C., "Current Concepts of Pelvic Congestion and Chronic Pelvic Pain," 2001 by JSLS, Journal of the Society of Laparoendoscopic Surgeons. Published by the Society of Laparoendoscopic Surgeons, Inc., 6 pages.
Howard, F., "Chronic Pelvic Pain," vol. 101, No. 3, Mar. 2003, 2003 by The American College of Obstetricians and Gynecologists. Published by Elsevier, 18 pages.

(Continued)

*Primary Examiner* — Jonathan Cwern
(74) *Attorney, Agent, or Firm* — Brinks Hofer Gilson & Lione

(57) ABSTRACT

A single device is provided for performing hysterography and intrauterine venography having a marker that aids in positioning the device within the patient, having a bulb-tip to seal the cervix, having a bulb-tip opening to allow an image enhancing medium to be discharged from a needle and injected into the uterus to perform the hysterography, having a needle to discharge and inject an image enhancing medium into the fundal myometrium to perform the intrauterine venography, and having a needle securing mechanism to secure the needle to prevent patient injury during transcervical introduction of the device.

14 Claims, 4 Drawing Sheets

OTHER PUBLICATIONS

Urology Tapes 1334-6, 2004 International Pelvic Pain Symposium transcription, 28 pages.

Nissel, J. "Hysterosalpingography," last updated Jul. 27, 2004, obtained at the Internet address http://my.webmd.com/hw/womens_conditions/aa16829.asp, dated Mar. 15, 2005, 6 pages.

Nissel, J. "Venography," last updated Apr. 1, 2004, obtained at the Internet address http://my.webmd.com/hw/health_guide_atoz/hw235506.asp, dated Mar. 15, 2005, 7 pages.

Cook®, Cook Urological, "Adapters, Connectors, Stopcocks, Caps and Handles," Cook Urological 2003, obtained at the Internet address http://www.cookurological.com/products/perc/4_05/4_05_02.html, 3 pages.

International Preliminary Report on Patentability dated Jan. 15, 2009 for related application No. PCT/US2007/014217.

* cited by examiner

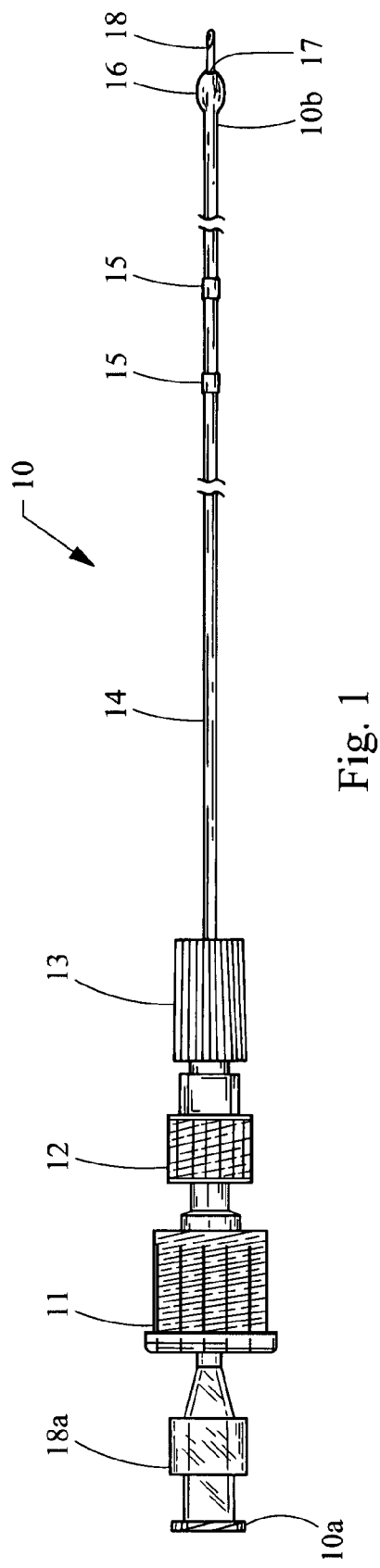
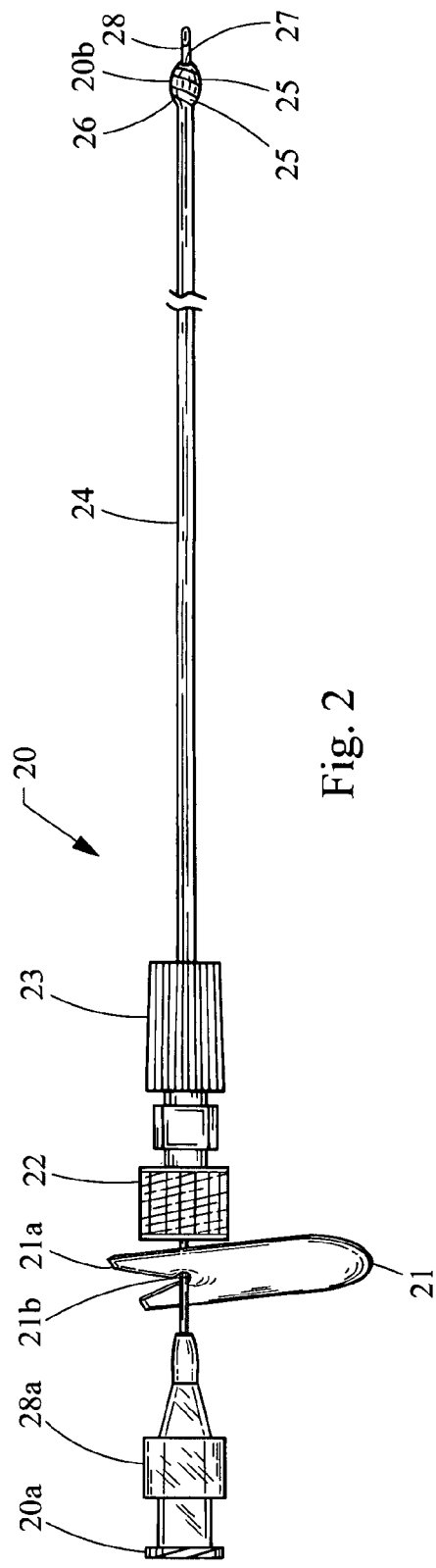
Fig. 1
Fig. 2

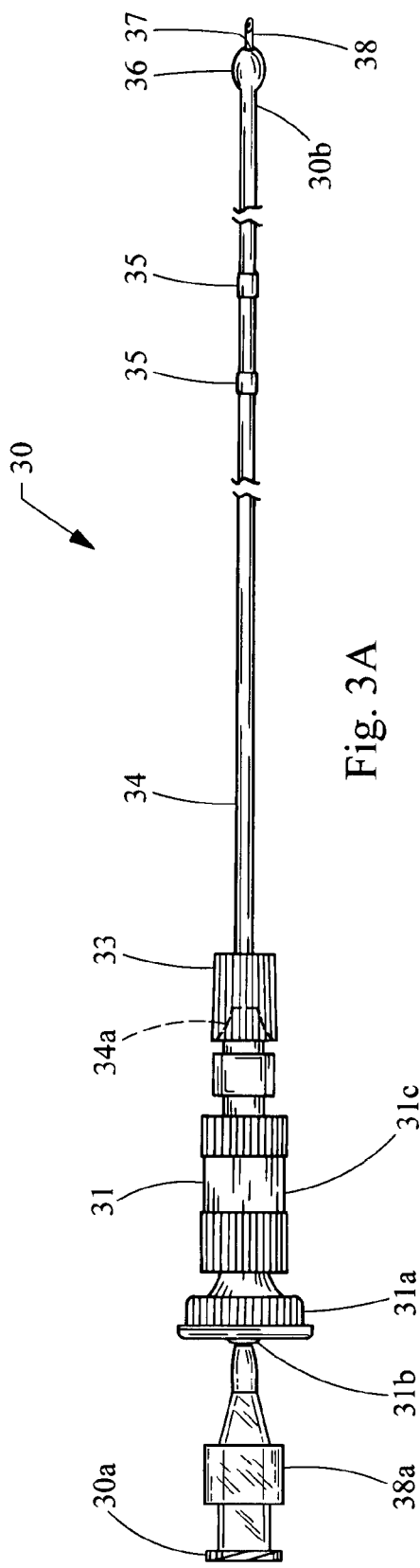
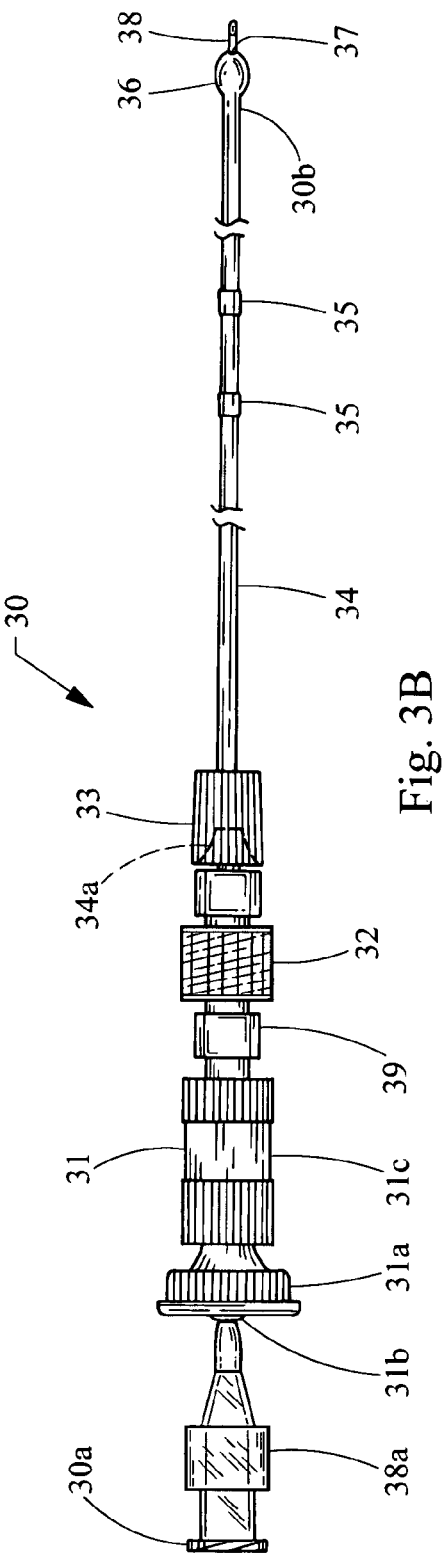
Fig. 3A
Fig. 3B

HYSTEROGRAPHY AND INTRAUTERINE VENOGRAPHY CATHETER

RELATED APPLICATIONS

The present patent document claims the benefit of the filing date under 35 U.S.C. §119(e) of Provisional U.S. Patent Application Ser. No. 60/816,719, filed Jun. 27, 2006, which is hereby incorporated by reference in its entirety.

FIELD OF THE INVENTION

This invention relates to diagnosis of uterine abnormalities, such as chronic pelvic pain and for performing diagnostic procedures such as hysterography and intrauterine venography.

BACKGROUND OF THE INVENTION

In order to diagnose a number of uterine problems, including chronic pelvic pain, the cause of which may include pelvic congestion, polyps, and tumors, e.g., submucous myomas, the use of diagnostic procedures known as hysterography and intrauterine venography are normally employed. Hysterography, also known as mapping of the uterus, is a procedure used to examine the inside of the uterus. It is performed by threading a catheter transcervically into the uterus. The uterus is sealed and an image enhancing medium is injected into the uterus to allow the inside of the uterus to be viewed and diagnosed by using a fluoroscope, ultrasound, x-ray, or other device or technique.

Intrauterine venography is a procedure used to examine the veins inside, surrounding, and leading from the uterus, specifically those that make up the fundal myometrium. To perform an intrauterine venography, a needle is threaded transcervically into the uterus and to the fundal myometrium. The needle pierces the fundal myometrium and an image enhancing medium is injected into the fundal myometrium. The medium allows the veins to be viewed and diagnosed by using a fluoroscope, ultrasound, x-ray, or other visualization device or technique.

A number of devices have been designed to perform hysterography and intrauterine venography. All of them require that these procedures be performed using multiple devices. The use of multiple devices may increase the patient's discomfort, the patient's recovery time, the amount of time necessary to complete the procedures, and may involve greater expense. A device is needed that will allow both hysterography and intrauterine venography to be performed without having to change and reinsert instruments.

BRIEF SUMMARY OF THE INVENTION

A device is provided for performing hysterography and intrauterine venography, the device including an elongated tubular body having a proximal portion and a distal portion; a bulb-tip having a bulb-tip opening, the bulb-tip assembled to the distal portion of the elongated tubular body; at least one marker located on the elongated tubular body or the bulb-tip; a needle positioned at least partially within the elongated tubular body; and a needle securing mechanism attached to the proximal portion of the elongated tubular body.

Further, a device is provided for performing a hysterography and intrauterine venography, the device including an elongated tubular body having a proximal portion and a distal portion; a connection cap attached to the elongated tubular body; a needle securing mechanism attached near the connection cap; a bulb-tip having a bulb-tip opening, the bulb-tip assembled to the distal portion of the elongated tubular body; two markers located on the elongated tubular body or the bulb-tip, the two markers set apart a known distance; and a needle positioned at least partially within the elongated tubular body.

Still further, a method for is provided for diagnosing uterine health, the method including inserting a device for performing hysterography and intrauterine venography transcervically into a uterus; determining a correct position of the device by using at least one marker on the device; discharging a first medium from a first syringe of the device and injecting the first medium into a uterus; viewing the uterus using a first diagnostic tool; advancing a needle of the device into a fundal myometrium of the uterus; discharging a second medium from a second syringe of the device through the needle and injecting the second medium into the fundal myometrium; and viewing the fundal myometrium using a second diagnostic tool.

Still further, a medical device is provided. The device includes an elongated tubular body having a proximal portion and a distal portion, a cervical seal assembled to the distal portion of the elongated tubular body, a needle positioned at least partially within the elongated tubular body, and a needle securing mechanism attached to the proximal portion of the elongated tubular body.

Further, a medical device is provided. The device includes an elongated tubular body having a proximal portion and a distal portion, a connection cap attached to the elongated tubular body, a needle securing mechanism attached near the connection cap, a cervical seal assembled to the distal portion of the elongated tubular body, two markers located on the elongated tubular body or the cervical seal, the two markers set apart a known distance, and a needle positioned at least partially within the elongated tubular body.

BRIEF DESCRIPTION OF THE SEVERAL VIEWS OF THE DRAWINGS

The embodiments will be further described in connection with the attached drawing figures. It is intended that the drawings included as a part of this specification be illustrative of the embodiments and should in no way be considered as a limitation on the scope of the invention.

FIG. 1 is a plan view of an embodiment of the device;

FIG. 2 is another plan view of an embodiment of the device;

FIGS. 3A-3B are plan views of embodiments of the device; and

DETAILED DESCRIPTION OF THE PRESENTLY PREFERRED EMBODIMENTS

Figure 4A:
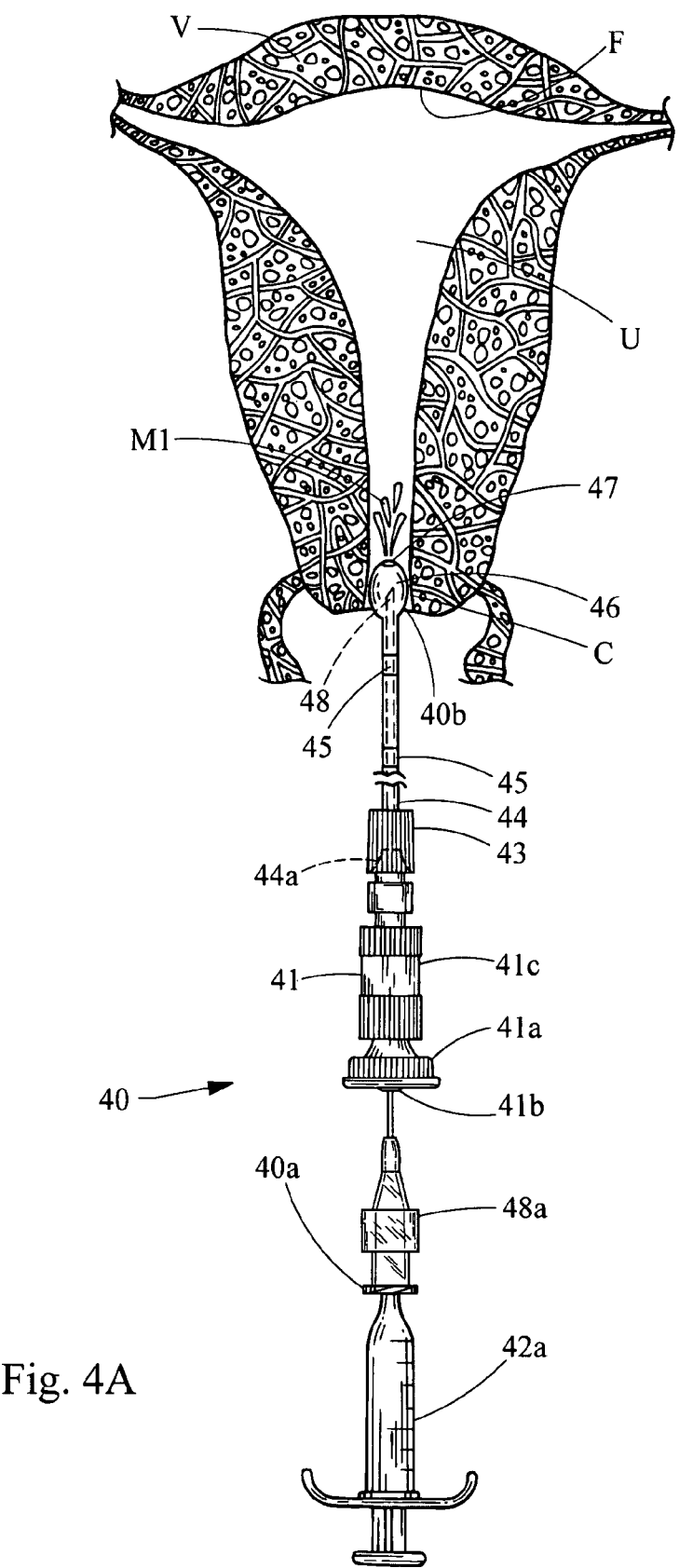
FIGS. 4A-4B are partial cross-sectional schematic front views of the intrauterine cavity depicting uses of the device.

The device provides a way to seal the uterus, a way to discharge an image enhancing medium into the uterus and fundal myometrium, and a way to determine the position of the device within the patient, which is not limited to a human being. Embodiments of the device provide an effective and safe procedure for performing hysterography and intrauterine venography. The embodiments are particularly useful for diagnosing uterine abnormalities, especially those associated with chronic pelvic pain, such as pelvic congestion.

A more detailed description of the embodiments will now be given with reference to FIGS. 1-4B. The present invention is not limited to those embodiments illustrated; it specifically contemplates other embodiments not illustrated but intended to be included in the claims. FIG. 1 is a plan view of a first embodiment. A catheter assembly embodiment 10 has a proximal portion 10a, a distal portion 10b, and an elongated tubular body 14 made from nylon, although elongated tubular body 14 may be made from other medically acceptable materials, including but not limited to, a polymer or a flexible metal. Elongated tubular body 14 has a lumen extending throughout. Elongated tubular body 14 has an outer diameter of 6 Fr. in order to fit through a cervix, although other diameters may be used. Distal portion 10b of catheter assembly 10 includes a bulb-tip 16 having a bulb-tip opening 17. Bulb-tip 16 seals the cervix and has an outer diameter of 9 Fr. and a height of 2.5 mm; other diameters may be used, and other heights may be used. The device is not limited for use with a bulb tip; other cervical seals may be used including, but not limited to, a cervical cone or wedge. Cervical seals are described in U.S. Pat. No. 6,706,026, assigned to the assignee of the present application, and incorporated by reference herein. The cervical seal need not fully occlude the cervix. Furthermore it is desired, but not required, that the seal be able to pass through the cervix because the seal acts as a leading edge to help move the distal end of the device through the cervix. The seal also acts as a limiting factor to help maintain contrast fluid within the cervix. Accordingly, it is likely, although not required, that at least some contrast fluid will escape from the uterus. A needle 18, used to deliver an image enhancing medium, extends throughout elongated tubular body 14, wherein needle hub assembly 18a is shown at proximal portion 10a of catheter assembly 10. Needle hub assembly 18a allows for a syringe (not shown) to be connected to catheter assembly 10. Needle 18 is an 18-gauge stainless steel extra thin-walled needle with a polycarbonate hub assembly 18a; other types of needles may be used. Proximal portion 10a of catheter assembly 10 comprises a Tuohy-Borst adapter 11 (available from Cook Urological, Spencer, Ind.) needle securing mechanism which is attached to a female luer lock adapter 12 which is attached to a connection cap 13. Tuohy-Borst adapter 11 includes a silicon gasket/septum (not shown) to prevent leakage or reflux of a medium once the medium is introduced through catheter assembly 10. Tuohy-Borst adapter 11 can be twisted and adjusted so that needle 18 remains within elongated tubular body 14 or bulb-tip 16 during transcervical placement or removal of catheter assembly 10 in order to avoid injuring the patient. Here, Tuohy-Borst adapter 11 is adjusted so that needle 18 extends out from bulb-tip opening 17. Distal portion 10b of catheter assembly 10 has two markers 15 made from Platinum-Iridium alloy or any other radiopaque or echogenic material, such as gold or tungsten. An echogenic material includes surface irregularities that reflect ultrasonic waves and thus, allow the material to be seen with ultrasonic imaging devices. Echogenic techniques are described in U.S. Pat. Nos. 5,081,997 and 5,289,831, assigned to the assignee of the present invention, and are hereby incorporated by reference in their entirety. Markers 15 are preferably set apart at a distance of 1 cm to aid in positioning catheter assembly 10 within the patient by determining the position of markers 15 using a fluoroscope or x-ray; other distances may be used, and other visualization devices or techniques may be used. Because markers 15 are set apart at a known distance, they can also aid in measuring the veins. The distal-most marker is set 4.5 cm from the distal portion of bulb-tip 16; other distances may be used, and the location of markers 15 is not limited to elongated tubular body 14. The length of catheter assembly 10 is 28 cm in order to reach the fundal myometrium; other lengths may be used. Further embodiments are shown in FIGS. 2-4B.

Referring now to FIG. 2 which depicts another plan view of an embodiment of the device. A catheter assembly 20 has a proximal portion 20a, a distal portion 20b, and an elongated tubular body 24. Elongated tubular body 24 has a lumen extending throughout. Distal portion 20b of catheter assembly 20 includes a bulb-tip 26 having a bulb-tip opening 27. A needle 28 extends through the elongated tubular body 24, wherein needle hub assembly 28a is shown at proximal portion 20a of catheter assembly 20. Distal portion 20b of catheter assembly 20 has two markers 25 which are placed on bulb-tip 26. Needle 28 is attached to a securing clip/holding pin 21 needle securing mechanism, which is attached to female luer lock adapter 22, and to a connection cap 23. Securing clip 21 is 1 inch long and has a height of 0.25 inches; other lengths and heights may be used. Securing clip 21 has a needle grasping mechanism 21a which has a diameter of 0.051 inches at its distal portion 21b; other diameters may be used. Needle grasping mechanism 21a is 0.25 inches long; other lengths may be used. Securing clip 21 includes a silicon gasket/septum (not shown) to prevent leakage or reflux of a medium once the medium is introduced through catheter assembly 20. The position of needle 28 is controlled by securing clip 21. Securing clip 21 can be adjusted so that needle 28 remains within elongated tubular body 24 or bulb-tip 26 during transcervical placement or removal in order to avoid injuring the patient. Here, securing clip 21 is adjusted so that needle 28 extends out from bulb-tip opening 27.

FIGS. 3A-3B are plan views of embodiments of the device. They show a catheter assembly 30 having an elongated tubular body 34 with a lumen extending throughout. Catheter assembly 30 has a proximal portion 30a and a distal portion 30b. Located at distal portion 30b are markers 35 and a bulb-tip 36 having a bulb-tip opening 37. A needle 38, having a needle hub assembly 38a, extends throughout elongated tubular body 34 that is connected through connection cap 33. At proximal portion 30a of catheter assembly 30 is a Check Flo Adapter 31 (available from Cook Urological, Spencer, Ind.) needle securing mechanism. Check Flo Adapter 31 has a cap 31a, a silicon retention disk septum 31b, and a Check Flo body 31c. Silicon retention disk septum 31b prevents leakage or reflux of a medium once the medium is introduced through catheter assembly 30. Silicon retention disk septum 31b also provides a constant frictional force on needle 38 to aid in securing the position of needle 38. For example, during transcervical placement or removal, needle 38 should remain within elongated tubular body 34 or bulb-tip 36 so as not to injure the patient. Here, needle 38 is shown pushed in the distal direction, and Check Flo Adapter 31 is used to maintain the position of needle 38 so that it protrudes out from bulb-tip opening 37 after having been positioned. To prevent patient injury during transcervical placement or removal, needle 38 is pulled in the proximal direction into elongated tubular body 34, and Check Flo Adapter 31 is used to maintain the position of needle 38 so that it does not protrude out from bulb-tip opening 37. Once catheter assembly 30 is positioned to perform the intrauterine venography, needle 38 is advanced in the distal direction through Check Flo Adapter 31 so that needle 38 may protrude out from bulb-tip opening 37 and be held in place via Check Flo Adapter 31.

FIG. 3B also shows a male luer lock adapter 39 connected to Check Flo Adapter 31 and female luer lock adapter 32. Based on the way Check Flo Adapter 31 is designed, the male luer lock adapter 39 and female luer lock adapter 32 are not essential because Check Flo Adapter 31 is capable of plugging directly into flared end 34a of elongated tubular body (as shown in FIG. 3A).

Figure 4B:
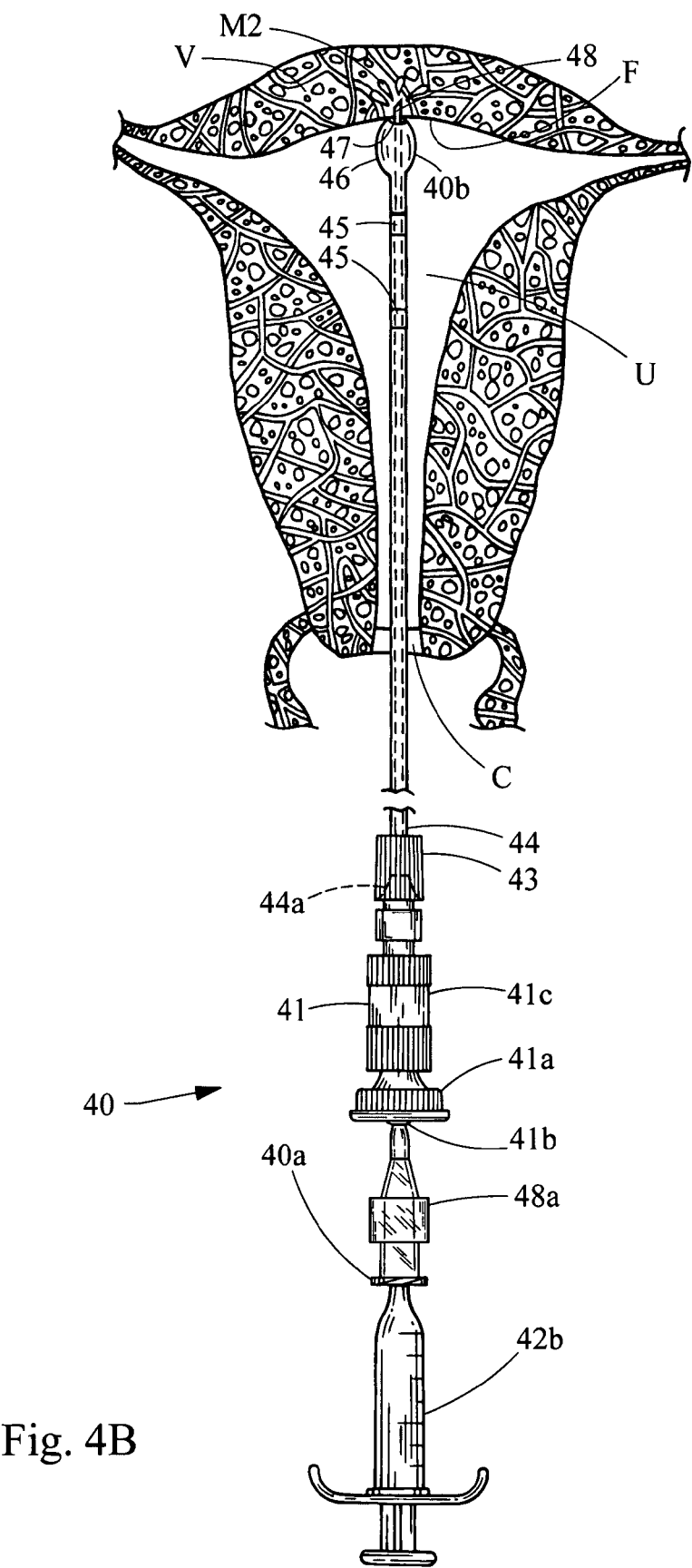

Now referring to FIGS. 4A-4B depicting schematic front views of the intrauterine cavity and uses of a catheter assembly embodiment 40 having a proximal portion 40a, a distal portion 40b, and an elongated tubular body 44 having a lumen extending throughout. Distal portion 40b of catheter assembly 40 has two markers 45. However, the use of more or less markers is contemplated. A needle 48 extends through the elongated tubular body 44, with needle hub assembly 48a extending at proximal portion 40a of catheter assembly 40. Needle 48 is attached to a Check Flo Adapter 41 (available from Cook Urological, Spencer, Ind.) needle securing mechanism, which is attached to the flared end 44a of elongated tubular body 44, which is then attached to a connection cap 43. Check Flo Adapter 41 has a cap 41a, a silicon retention disk septum 41b, and a Check Flo body 41c. Silicon retention disk septum 41b prevents leakage or reflux of a medium once the medium is introduced through catheter assembly 40. Silicon retention disk septum 41b also provides a constant frictional force on needle 48 to aid in securing the position of needle 48. Needle 48 is pulled in the proximal direction through Check Flo Adapter 41 so that needle 48 remains within elongated tubular body 44 or bulb-tip 46 while catheter assembly 40 is being transcervically introduced.

The device may be utilized to deliver a therapeutic agent into uterus U and fundal myometrium F. Continuing to refer to FIGS. 4A-4B, the device is utilized to perform a hysterography and intrauterine venography for the purpose of diagnosing chronic pelvic pain. A first syringe 42a is preloaded with 10 ml of image enhancing medium M1 that is radiopaque to perform the hysterography; other image enhancing media M1 may be used, and other quantities of image enhancing medium M1 may be used. A second syringe 42b and a third syringe (not shown) are each preloaded with 5-10 ml of a medically acceptable water-soluble image enhancing medium M2 that is radiopaque that is used for performing intrauterine venography; other medically acceptable image enhancing media M2 may be used, and other quantities of image enhancing medium M2 may be used. The type and amount of image enhancing medium M1 used to perform the hysterography may be the same or different from the image enhancing medium M2 used to perform intrauterine venography. Although three separate syringes be used to perform the procedures, a fewer or great number of syringes can be used.

Referring to FIG. 4A, to perform the hysterography, first syringe 42a is connected to needle hub assembly 48a of needle 48. Before transcervical placement of catheter assembly 40, needle 48 is pulled in the proximal direction through Check Flo Adapter 41 so that needle 48 is positioned within elongated tubular body 44 or bulb-tip 46 to prevent patient injury during transcervical introduction of catheter assembly 40. The positioning of catheter assembly 40 within the patient is determined by use of two markers 45 using a fluoroscopic, ultrasound, x-ray, or other visualization device or technique. Distal portion 40b of catheter assembly 40 is transcervically threaded into uterus U. When bulb-tip 46 passes the cervix C and enters uterus U, a pop is felt. Catheter assembly 40 is then pulled back so that bulb-tip 46 seals cervix C. Image enhancing medium M1 is discharged from first syringe 42a into non-extended needle 48 through the bulb-tip opening 47 and injected into uterus U. Uterine health may be evaluated by fluoroscopy, sonography, x-ray, or other medically acceptable visualization devices or techniques. A device is used to evaluate uterine health that captures images in a single instance of time or at time intervals of 0, 20, 40, 60, and 80 seconds. Any remaining image enhancing medium M1 is removed from uterus U using first syringe 42a. First syringe 42a is then removed from the device.

To perform the intrauterine venography, as shown in FIG. 4B, second syringe 42b is connected to needle hub assembly 48a of needle 48. Catheter assembly 40 is advanced within the patient to the midline fundal wall F. The position of catheter assembly 40 is determined by using markers 45; the location of markers 45 is determined by using a fluoroscopic, ultrasound, or x-ray; other visualization devices or techniques may be used. Fundal myometrium F is reached when a bump is felt. Needle 48 is advanced in the distal direction through Check Flo Adapter 41 so that it extends out from bulb-tip opening 47. Check Flo Adapter 41 holds needle 48 in place so that needle 48 does not slip back into bulb-tip 46 or elongated tubular body 44. Needle 48 is advanced into fundal myometrium F so that needle 48 is embedded 2-3 mm (other distances can be used) into fundal myometrium F or until proximal portion 40a of catheter assembly 40 and needle hub assembly 48a are coupled. Image enhancing medium M2 is discharged from each of second syringe 42b, and third syringe (not shown) into needle 48 and injected into the veins V surrounding and comprising fundal myometrium F under fluoroscopic or x-ray guidance; other visualization devices or techniques may be used. Vein V patency is evaluated by using a fluoroscope or x-ray that captures an image at a single instance of time or at time intervals of 0, 20, 40, 60, and 80 seconds; other visualization devices or techniques may be used, and other time intervals may be used. Needle 48 is then pulled in the proximal direction through Check Flo Adapter 41 so that needle 48 is positioned inside bulb-tip 46 or elongated tubular body 44. To avoid patient injury, Check Flo Adapter 41 holds needle 48 in place so that needle 48 will not extend out from bulb-tip 46 or elongated tubular body 44. Catheter assembly 40 is then removed from the patient.

As is evident, the embodiments provide a very effective design for performing hysterography and intrauterine venography; the prior art devices required that these two procedures be performed using more than one device. Moreover, markers 45 provide the advantage of aiding in positioning catheter assembly 40 within the patient and the ability to measure veins V. The needle securing mechanism (including, but not limited to, Check Flo Adapter 41, Tuohy-Borst adapter 11 (as shown in FIG. 1), and securing clip 21 (as shown in FIG. 2)), provides the advantage of being able to control the position of needle 48 and whether or not needle 48 extends out from bulb-tip opening 47 to avoid injuring the patient. Bulb-tip 46 provides the advantage of sealing cervix C so that an image enhancing medium M1 may be discharged from needle 48 through bulb-tip opening 47 and injected into uterus U to perform the hysterography. Needle 48 also provides the advantage of discharging image enhancing medium M2 into fundal myometrium F so that the intrauterine venography can be performed.

The foregoing description and drawings are provided for illustrative purposes only and are not intended to limit the scope of the invention described herein or with regard to the details of its construction and manner of operation. It will be evident to one skilled in the art that modifications and variations may be made without departing from the spirit and scope of the invention. Changes in form and in the proportion of parts, as well as the substitution of equivalents, are contemplated as circumstances may suggest and render expedience; although specific terms have been employed, they are intended in a generic and descriptive sense only and not for the purpose of limiting the scope of the invention set forth in the following claims.

The invention claimed is:

1. A method for diagnosing uterine health, the method comprising:
inserting a device configured for performing hysterography and intrauterine venography transcervically into a uterus, the device comprising a catheter and a needle movably disposed through a lumen within the catheter, wherein a tip of the needle is fixably maintained within the lumen during the inserting step;
determining a correct depth of the device within the uterus by remote observation of at least one marker on the device with the first diagnostic tool;
discharging a first medium configured for enhancing the hysterography from a first syringe into the device and injecting the first medium into the uterus;
viewing the uterus using a first diagnostic tool for performing hysterography;
advancing the needle of the device into a fundal myometrium of the uterus;
discharging a second medium configured for enhancing the venography from a second syringe into the needle and injecting the second medium into the fundal myometrium; and
viewing the fundal myometrium using a second diagnostic tool for performing the venography.

2. The method according to claim 1 wherein about 5-10 ml of the first medium is discharged and about 10-20 ml of the second medium is discharged.

3. The method according to claim 1 further comprising discharging about 10 ml of the second medium from each of the second syringe and a third syringe of the device through the needle.

4. The method according to claim 1 wherein the first medium and the second medium are image enhancing media and are the same or different.

5. The method according to claim 1 wherein the first diagnostic tool and the second diagnostic tool are a fluoroscope, x-ray, or ultrasound, and are the same or different.

6. The method according to claim 1 further comprising sealing the cervix by using a bulb-tip of the device.

7. The method according to claim 1 wherein the first syringe and the second syringe are the same or different.

8. The method according to claim 1 further comprising a securing mechanism disposed at a proximal end portion of the catheter, wherein the securing mechanism is configured to be adjustable between a first orientation fixing the position of the needle with respect to the catheter and a second orientation allowing the needle to slide within the lumen and out of a distal end of the catheter.

9. The method according to claim 8 further comprising locking the needle with respect to the catheter with the securing mechanism prior to inserting the device into the uterus.

10. The method according to claim 9 further comprising unlocking the needle with respect to the catheter with the securing mechanism prior to advancing the needle into the fundal myometrium of the uterus.

11. The method according to claim 9 further comprising unlocking the needle with respect to the catheter with the securing mechanism after a distal end of the catheter contacts the fundal myometrium.

12. The method according to claim 1 where the at least one marker on the device comprises two markers upon a distal portion of the catheter, wherein the two markers are spaced at a fixed distance apart and are each remotely observable with the first diagnostic tool.

13. The method according to claim 12 wherein the two markers upon the distal portion of the catheter are each radiopaque or echogenic.

14. The method according to claim 12 further comprising the step of measuring aspects of the fundal myometrium based upon comparison of the relative positioning and distance of the two markers with remotely observable aspects of the fundal myometrium using the second diagnostic tool.

* * * * *